United States Patent [19]

Machida

[11] 4,344,937

[45] Aug. 17, 1982

[54] ANTIVIRAL AGENT COMPRISING 1-β-D-ARABINOFURANOSYLTHYMINE

[75] Inventor: Haruhiko Machida, Choshi, Japan

[73] Assignee: Yamasa Shoyu Kabushiki Kaisha, Choshi, Japan

[21] Appl. No.: 182,001

[22] Filed: Aug. 28, 1980

[30] Foreign Application Priority Data

Sep. 5, 1979 [JP] Japan .................. 54-112990

[51] Int. Cl.$^3$ .............................................. A61K 31/70
[52] U.S. Cl. .................................................... 424/180
[58] Field of Search ........................... 536/23; 424/180

[56] References Cited

U.S. PATENT DOCUMENTS

| | | | |
|---|---|---|---|
| 3,998,807 | 12/1976 | Moffatt | 536/23 |
| 4,145,414 | 3/1979 | Kelly et al. | 536/23 |
| 4,230,698 | 10/1980 | Bobek et al. | 536/23 |

OTHER PUBLICATIONS

Cermak-Mörth, C., et al., Biochemical Pharmacology, vol. 28, pp. 2105–2108, 1979.

Lefkowitz, E., et al., Proc. Soc. Exp. Biol. Med., vol. 152, pp. 337–342, 1976.

Neil, G., et al., Cancer Research, vol. 30, pp. 2166–2172, 1970.

Ho, D., et al., Clinical Pharmacology and Therapeutics, vol. 12, pp. 944–954 (1951).

Chemical Abstracts, vol. 87, p. 42, 1977, Abst. No. 177682w, "Antiviral activity of arabinosylthymine in herpesviral, replication; mechanism of action in vivo and in vitro".

Chemical Abstracts, vol. 87, p. 161, 1977, Abst. No. 169h, "Arabinosylthymine, a selective antiherpes agent".

Machida, H., et al., Antimicrobial Agents and Chemotherapy, vol. 17, pp. 109–114, 1980.

Gray, G., et al., Biochemical Pharmacology, vol. 21, pp. 465–475, 1972.

Aswell, J. F., et al., Antimicrobial Agents and Chemotherapy, vol. 12, pp. 243–254, 1977.

Primary Examiner—Blondel Hazel
Attorney, Agent, or Firm—Wenderoth, Lind & Ponack

[57] ABSTRACT

An antiviral agent comprising 1-β-D-arabinofuranosylthymine as a therapeutically efficacious component in a pharmaceutical form for absorption through the alimentary canal of the human or lower animal to be treated.

3 Claims, No Drawings

ANTIVIRAL AGENT COMPRISING 1-β-D-ARABINOFURANOSYLTHYMINE

BACKGROUND OF THE INVENTION

This invention relates generally to antiviral agents and more particularly to a new antiviral agent comprising 1-β-D-arabinofuranosylthymine as a therapeutically efficacious component and prepared in a pharmaceutical form for absorption through the alimentary canal of the human or lower animal to be treated.

Representative examples of antiviral agents heretofore known are 5-iodo-2'-deoxyuridine (hereinafter referred to by the abbreviation "IDU") and 9-β-D-arabinofuranosyladenine (hereinafter abbreviated "ara-A"). IDU, however, produces side effects such as teratosis and by no means can be said to be a safe antiviral agent. Similarly as in the case of IDU, ara-A also strongly inhibits growth of animal cells including those of humans and is also reported to give rise to teratosis, whereby its toxicity is a cause of concern when it is employed as a medicinal remedy.

On one hand, 1-β-D-arabinofuranosylthymine (hereinafter abbreviated "ara-T") is known to exhibit high antiviral activity in vitro against herpes simplex virus (HSV) and varicella-zoster virus (VZV) as reported in *Virology*, Vol. 65, p. 294 through p. 296 (1975); *Antimicrobial Agents and Chemotherapy*, Vol. 12, p. 243 through p. 254 (1977); and *Journal of Virology*, Vol. 23, p. 679 through p. 684 (1977). As for the antiviral activity in vivo of ara-T, the only report I am aware of is that concerning a therapeutic experiment with hamsters infected with equine abortion virus (EAV). See *Antimicrobial Agents and Chemotherapy*, Vol. 12, p. 243 through p. 254 (1977); and Annals, New York Academy of Science, Vol. 284, p. 342 through p. 350 (1977).

Anti-DNA virus agents used for clinical treatments or undergoing clinical experiments at present are being administered by non-oral methods such as intravenous administration, and there appear to be none that are effective when administered orally. It is considered that, in general, an inhibitor of DNA synthesis exhibits its efficacy more when administered by a non-oral method than when it is administered orally. Therefore, an antiviral activity test in vivo of ara-T is also being carried out by non-oral administration such as intraperitoneal administration, and there have been no reports whatsoever of its oral administration.

As a result of various studies I have carried out with the aim of developing antiviral agents of high efficacy yet low toxicity, I discovered that, when ara-T was administered orally, it exhibited a much more effective antiviral activity and less toxicity than when administered by a non-oral method, and, therefore, a ratio of its tolerance dosage to the effective concentration for treatment became much greater. Furthermore, it was also verified that, when ara-T was orally administered to mice, it was absorbed through the digestive system and was retained at a considerably high concentration in the blood for a definite time.

Accordingly, it was confirmed that the method of orally administering ara-T thereby to cause it to be absorbed into the body through the alimentary canal is an extremely effective method of treating DNA viral infections.

SUMMARY OF THE INVENTION

This invention is based on and has been developed from these findings. More specifically, this invention relates to a new form of preparation of ara-T used in carrying out the method of treating viral infections such as DNA viral infections by causing ara-T to be absorbed through the alimentary canal.

According to this invention, briefly summarized, there is provided an antiviral agent which comprises 1-β-D-arabinofuranosylthymine as a therapeutically efficacious component and prepared in a pharmaceutical form for absorption through the alimentary canal of the human or lower animal.

The nature, utility, and further features of this invention will be more apparent from the following detailed description beginning with a consideration of general and basic aspects of the invention and concluding with examples of experiments relating to therapy, to toxicity, and to metabolism.

DETAILED DESCRIPTION OF THE INVENTION

In this invention, "a pharmaceutical form for absorption through the alimentary canal" includes the dosage forms for the oral administration and the administration through the rectum.

Examples of the forms of doses for the oral administration are tablets, capsules, soft elastic capsules, granules, slow-release granules, fine grains, powder, and syrup. Carriers and additives such as excipients, diluents, coating agents, binders, disintegrators, lubricants, preservatives, perfumes, coloring matter, seasoning agents, and other additive agents to be used in compounding these agent forms are appropriately selected and blended in accordance with the kind of the agent forms. Ordinary compounding methods are used.

The dosage of ara-T per day for an adult in the orally administered agent is ordinarily within the range of 500 to 50,000 mg., preferably 1,000 to 10,000 mg. While the therapeutic dose per pharmaceutical unit differs with the kind of pharmaceutic process and administering schedule, it is ordinarily and preferably from 100 to 500 mg.

Examples of the forms for the administration through the rectum are suppositories. For bases used in suppositories, generally used bases are used, and ordinary compounding methods are used.

In order to indicate fully the nature and utility of this invention, the following examples of experiments relating to therapy, toxicity, and metabolism are set forth, it being understood that these examples are presented as illustrative only and are not intended to limit the scope of the invention.

I. THERAPY EXPERIMENTS

Each of 10 mice in one treatment group and 20 mice in one control group (ICR-JCL strain four-week-old mice) was inoculated intracerebrally with 10 $LD_{50}$ (50% lethal dose) of herpes simplex virus (HSV). Treatment was started 4 hours thereafter. The states of life or death of the mice were observed for 21 days. The control group was treated with phosphate-buffered saline (PBS), and the mean survival times (days) and survival rates were compared. The results relating to mice surviving 21 days or longer were not included in the calculation of the mean survival times, and the test of the significant difference relative to the control group was according to the t-test. The test of the significant difference of survival rate was according to the Fisher exact test.

While, in each example of experiment, the efficacy of treatment against infection with HSV type 1 (HSV-1) is indicated, it is confirmed that ara-T is effective also against infection with HSV type 2 with an efficacy of the same order as that against infection with HSV-1.

EXPERIMENT 1

Starting from 4 hours after infection with HSV-1, ara-T was orally administered every 12 hours for a total of 9 treatments. As indicated by the results set forth in Table 1, a significant increase in life span (ILS) was observable at an administered quantity of 100 mg/kg × 9, and both an ILS and a rise in survival rate were significantly detectable at an administered quantities of 200 mg/kg and greater × 9.

TABLE 1

| Quantity administered (mg/kg × 9) | Survivors/total treated | Mean survival time (days) ± standard error |
|---|---|---|
| 0 | 1/18 | 4.0 ± 0.13 |
| 100 | 3/9 | 8.0 ± 0.71[b] |
| 200 | 5/9[a] | 7.5 ± 0.65[b] |
| 400 | 5/9[a] | 6.0 ± 1.08[a] |
| 800 | 7/9[b] | 9.5 ± 0.50[b] |

[a]Probability value < 0.01
[b]Probability value < 0.001

EXPERIMENT 2

With the same treatment schedule as in Experiment 1, comparison was made with the effect due to intraperitoneal administration. As is apparent from the results shown in Table 2, the minimum effective quantity in intraperitoneal administration is 40 mg/kg × 9, whereas that in oral administration is not more than 27 mg/kg × 9. Thus, oral administration had a greater effect than intraperitoneal administration.

TABLE 2

| Route of administration | Quantity administered (mg/kg × 9) | Survivors/total treated | Mean survival time (days) ± standard error |
|---|---|---|---|
| p.o. (orally) | 0 | 0/9 | 4.3 ± 0.26 |
| | 27 | 2/9 | 6.6 ± 0.74[b] |
| | 40 | 2/9 | 7.6 ± 0.57[c] |
| | 60 | 1/9 | 6.8 ± 0.48[c] |
| | 90 | 3/9 | 7.4 ± 0.24[c] |
| i.p. (intraperitoneally) | 0 | 0/10 | 4.7 ± 0.37 |
| | 27 | 0/10 | 5.7 ± 0.45 |
| | 40 | 0/10 | 5.8 ± 0.33[a] |
| | 60 | 2/10 | 6.8 ± 0.56[b] |
| | 90 | 2/10 | 6.8 ± 0.75[a] |

[a]Probability value < 0.05
[b]Probability value < 0.01
[c]Probability value < 0.001

EXPERIMENT 3

Eight hours after infection with HSV-1, treatment was carried out only once, and the efficacy of the treatment was investigated. As indicated by the results shown in Table 3, no increase in the number of surviving mice was observable, but the ILS due to oral administration was much more remarkable than that due to intraperitoneal administration.

TABLE 3

| Route of administration | Quantity administered (mg/kg) | Mean survival time (days) (treated group/control group) |
|---|---|---|
| p.o. | 400 | 1.35[b] |
| | 800 | 1.67[c] |
| i.p. | 400 | 1.12 |
| | 800 | 1.24[a] |

[a]Probability value < 0.05
[b]Probability value < 0.01
[c]Probability value < 0.001

EXPERIMENT 4

Starting from 4 hours after infection with HSV-1, ara-T was administered every 48 hours for a total of 5 treatments. As indicated by the results set forth in Table 4, and ILS was evident with each of doses of 100, 200, and 400 mg/kg/treatment, but intraperitoneal administration did not produce any efficacy even at a dose of 400 mg/kg/treatment.

TABLE 4

| Route of administration | Quantity administered (mg/kg/treatment) | Survivors/total treated | Mean survival time (days) ± standard error |
|---|---|---|---|
| p.o. | 100 | 1/10 | 5.8 ± 0.6[a] |
| | 200 | 1/10 | 6.1 ± 0.6[b] |
| | 400 | 0/10 | 5.8 ± 0.5[a] |
| i.p. | 200 | 1/10 | 5.4 ± 0.8 |
| | 400 | 0/10 | 5.0 ± 0.5 |
| Control | — | 0/20 | 4.3 ± 0.3 |

[a]Probability value < 0.02
[b]Probability value < 0.01

II. TOXICITY EXPERIMENTS

In varied therapeutic doses, ara-T was administered orally to some mice (ICR strain) and intraperitoneally to other mice of the same strain to be subjected to an acute toxicity test. The mice were observed for one week. As a result, $LD_{50}$ in the case of oral administration was higher than 15 g/kg (zero deaths among 10 mice at 15 g/kg) and in the case of intraperitoneal administration was higher than 10 g/kg (2 fatalities among 10 mice at 10 g/kg). Furthermore, body weight reduction and thymic atrophy were observed at 10 g/kg in the case of intraperitoneal administration, whereas neither was observed at 15 g/kg in the case of oral administration.

In addition, ara-T in varied doses was administered to four-week-old mice every 12 hours for a total of 9 administrations, and the mice thus treated were observed for one week thereafter. The resulting relationship between the administration quantity and the mortality rate was as indicated in Table 5.

TABLE 5

| Route of administration | Quantity administered (g/kg × 9) | Mortality (No. dead/total treated) |
|---|---|---|
| p.o. | 1.5 | 0/5 |
| | 3 | 0/5 |
| | 6 | 1/5* |
| i.p. | 1 | 0/5 |
| | 2 | 3/5* |
| | 4 | 5/5* |

*Great reduction of body weight was observed.

III. METABOLISM EXPERIMENTS

A study was made with the aim of determining whether or not ara-T which has been orally administered is actually absorbed and transferred into the blood.

Ara-T was orally administered in a quantity of 200 mg/kg to mice. After a suitable time period, blood samples were taken from the hearts of the mice, and the concentration of ara-T in the plasma of each sample was measured in a high-speed liquid chromatograph. The results thus obtained are shown in Table 6, in which each measured value is the average value of one group comprising four mice. As is apparent from Table 6, ara-T was absorbed well through the alimentary canal, and its concentration in the blood amply rose. Furthermore, the absorption continued up to two hours after administration, and the concentration of the ara-T in blood was sustained for a long time at a high value. (A minimal inhibitory concentration of ara-T against HSV in vitro is a concentration of 1 μg/ml).

TABLE 6

| Hours after administration (hr) | Concentration of ara-T in blood (μg/ml) |
| --- | --- |
| 0.5 | 25 |
| 1 | 33 |
| 2 | 21 |
| 3 | 13 |
| 4 | 12 |
| 6 | 3 |
| 8 | 1 |

As described above, when the antiviral agent of this invention is administered in a pharmaceutical form for absorption through the alimentary canal, it boosts the already known activity of ara-T, moreover, greatly reduces the toxicity thereof, and is effective in the treatment of infection with DNA viruses such as herpes virus group including HSV and VSV in mammals.

More specific pharmaceutical forms of this antiviral agent are appropriately selected in accordance with factors such as the kind of DNA viral infection, degree of the symptoms, and administration schedule. Furthermore, the corresponding compounding method can be readily selected and practiced by those skilled in the art from known facts and by ordinary techniques.

One example of a pharmaceutical form of the antiviral agent of this invention is presented below.

| Pharmaceutical example (tablet) | |
| --- | --- |
| ara-T | 200 mg |
| lactose | 191 mg |
| starch | 50 mg |
| polyvinyl pyrolidone | 5 mg |
| magnesium stearate | 4 mg |
| Total weight | 450 mg |

It is to be understood that the modes of practice of this invention are not limited to the above example, various compounding designs being possible on the basis of the therapeutic doses as described hereinbefore. Furthermore, the combined use of the antiviral agent of this invention with another antivirally active substance is also possible.

What is claimed is:

1. A method of treating DNA viral infections in humans or lower animals which comprises administering a pharmaceutically efficacious quantity of 1-$\beta$-D-arabinofuranosylthymine to a human or lower animal in need of such treatment through the alimentary canal thereof.

2. The method as claimed in claim 1 in which the administration is made orally.

3. The method as claimed in claim 1 in which the administration is made through the rectum.

* * * * *